United States Patent
Agrawal et al.

(10) Patent No.: US 9,403,995 B2
(45) Date of Patent: Aug. 2, 2016

(54) BLUE COLOURED AQUEOUS DISPERSION OF SILVER NANOPARTICLES A PROCESS FOR PREPARATION AND COMPOSITIONS THEREOF

(75) Inventors: Ashwini K. Agrawal, New Delhi (IN); Manjeet Jassal, New Delhi (IN); Sangita Paul, New Delhi (IN); Ganesh Srinivasan, Karnataka (IN); Gayatri Hela Pamidipati, Karnataka (IN)

(73) Assignees: Indian Institute of Technology, Delhi (IN); Resil Chemicals Private Limited, India (IN)

( * ) Notice: Subject to any disclaimer, the term of this patent is extended or adjusted under 35 U.S.C. 154(b) by 368 days.

(21) Appl. No.: 13/882,211

(22) PCT Filed: Nov. 2, 2011

(86) PCT No.: PCT/IN2011/000758
§ 371 (c)(1), (2), (4) Date: Sep. 10, 2013

(87) PCT Pub. No.: WO2012/059944
PCT Pub. Date: May 10, 2012

(65) Prior Publication Data
US 2014/0005295 A1    Jan. 2, 2014

(30) Foreign Application Priority Data
Nov. 2, 2010 (IN) ............................. 2629/DEL/2010

(51) Int. Cl.
*B01J 13/00* (2006.01)
*C09D 5/14* (2006.01)
*A01N 59/16* (2006.01)
*D06M 11/83* (2006.01)
*D06M 16/00* (2006.01)
*D06M 23/08* (2006.01)

(52) U.S. Cl.
CPC *C09D 5/14* (2013.01); *A01N 59/16* (2013.01); *B01J 13/0043* (2013.01); *D06M 11/83* (2013.01); *D06M 16/00* (2013.01); *D06M 23/08* (2013.01)

(58) Field of Classification Search
CPC ......... C09D 5/14; A01N 59/16; D06M 11/83; D06M 16/00; D06M 23/08; B01J 13/0043
See application file for complete search history.

(56) References Cited

U.S. PATENT DOCUMENTS 2,806,798 A * 9/1957 Weaver ................ B01J 13/0043
106/1.05
2008/0064767 A1 * 3/2008 Chou ................... B01J 13/0043
516/97

FOREIGN PATENT DOCUMENTS

WO    WO 2009056401 A1 * 5/2009 ................ B22F 9/24

OTHER PUBLICATIONS

Machine translation of KR 10-0933736 B1, published Dec. 16, 2009.*

* cited by examiner

*Primary Examiner* — Vickey Nerangis
(74) *Attorney, Agent, or Firm* — Luedeka Neely Group, PC (57) ABSTRACT

The present invention provides blue colored aqueous dispersion of silver nanoparticles and process for preparation thereof. The present invention also provides compositions comprising blue colored dispersion of silver nanoparticles. The blue colored aqueous dispersion comprising silver nanoparticles wherein dispersion is characterized by —having plasmonic peaks in the range 330-335 nm and 650-720 nm combined with missing plasmonic peaks in the range 390 to 410 nm and 410-500 nm in UV-Vis spectrum, —the dispersion having silver nanoparticles of anisotropic shape with majority of particles (>65%) having equivalent diameter in range of 0.5 to 6 nm, —Molar extinction coefficient greater than 10.1 preferably in the range of 10.1 to 15.7 $mM^{-1}\ cm^{-1}$ at wavelength of maximum absorption in the range of 650-720 nm, —Dispersion stability of at least 15 months, —Minimum Bactericidal Concentration (MBC) lower than 0.10 ppm preferably in the range of 0.055-0.099 ppm.

24 Claims, 4 Drawing Sheets

BLUE COLOURED AQUEOUS DISPERSION OF SILVER NANOPARTICLES A PROCESS FOR PREPARATION AND COMPOSITIONS THEREOF

FIELD OF THE INVENTION

The present invention provides blue coloured aqueous dispersion of silver nanoparticles and process for preparation thereof. The present invention also provides compositions comprising blue coloured dispersion of silver nanoparticles.

BACKGROUND OF THE INVENTION

The description of the prior art given below is only indicative and is not meant to be exhaustive.

Nanosilver is a highly potent antimicrobial agent. The state-of-the-art antimicrobial finishes based on nano silver are yellow to dark brown in colour depending upon the silver concentration. When these silver nanodispersions are applied to textile or polymeric substrates, it often results in poor aesthetics in terms of lower Whiteness Index or higher Yellowness Index, which is undesirable primarily for white and pale shade garments or substrates.

The problem of colour is further aggravated as nanosilver dispersions are required to be applied on textiles/substrate at high concentration for effective antimicrobial activity (>80%). The Minimum Bactericidal Concentration (MBC) values for dispersions of silver nanoparticles are in the range of 5-1000 ppm (references given in text below), which is quite high. The silver is a precious metal and its application at higher concentration is commercially undesirable.

Also, the dispersions of nanosilver based finishes available in prior art are non durable. The nanoparticles tend to agglomerate and settle down with time in the dispersion form giving poor shelf life. Several additives used for stabilizing these nanofinishes often impart still deeper colours to the nano dispersion making it undesirable. When applied on substrates they lose their efficacy on repeated washing as the silver nano particles or their agglomerate tends to wash off the substrate. If binders are used, the nanosilver loses its high degree of activity against the bacteria.

The synthesis techniques of silver nanoparticles are categorized into bottom-up and top-down approaches. Some of the important approaches are listed below:

Bottom-up approach can be used with the following methods:

Chemical reduction method. This involves the dissolution of silver salt into a solvent (aqueous or non-aqueous) and subsequent addition of a suitable reducing agent e.g. chemical reduction of silver ion in aqueous solutions or non-aqueous solutions (Maribel G. Guzmán, Jean Dille, Stephan Godet, World Academy of Science, Engineering and Technology 43 2008; Zaheer Khan, Shaeel Ahmed Al-Thabaiti, Abdullah Yousif Obaid, A. O. Al-Youbi, Colloids and Surfaces B: Biointerfaces 82 (2011) 513-517; CHEN Yanming Li, CN1994633; Sun, Rong; Zhao, Tao; Yu, Shuhui; Du, Ruxu, CN 102085574).

Template method (Shinsuke Ifuku, Manami Tsuji, Minoru Morimoto, Hiroyuki Saimoto, and Hiroyuki Yano *Biomacromolecules* 2009, 10, 2714-2717). This process involves synthesizing a desired material within the pores of a porous membrane.

Electrochemical or ultrasonic-assisted reduction (N. Perkas, G. Amirian, S. Dubinsky, S. Gazit, A. Gedanken, Journal of Applied Polymer Science, Vol. 104, 1423-1430 (2007)). The chemical effects of ultrasound arise from acoustic cavitation, that is, the formation, growth, and when solutions are exposed to strong ultrasound irradiation, bubbles in the solution are implosively collapsed by acoustic fields. Cavitation bubble collapse can also induce a shock wave in the solution and drive rapid impact of the liquid to the surface of the particles.

Photoinduced or photocatalytic reduction (C. C. Chang, C. K. Lin, C. C. Chan, C. S. Hsu, C. Y. Chen, Thin Solid Films 494 (2006) 274-278; Lizhi Zhang, Jimmy C. Yu, Ho Yin Yip, Quan Li, Kwan Wai Kwong, An-Wu Xu, and Po Keung Wong, Langmuir 2003, 19, 10372-10380; Wu Juan, Zhang Hongbin, CN 102198511). It takes very long time (sometimes over 70 hours, R Jin, Y Wei Cao and C A. Mirkin, SCIENCE 294 (2001)). The photoprocess involves surface plasmon excitation, and this feature allows one to tailor the size and shape of the disks by simply varying the irradiation wavelength.

Microwave (MW)-assisted synthesis (K J Sreeram, M Nidhin and B U Nair, Bull. Mater. Sci., Vol. 31, No. 7, December 2008, pp. 937-942). MW provides rapid and uniform heating of reagents, solvents, intermediates, and products. Fast heating accelerates the reduction of metal precursors and the nucleation of the metal cluster, resulting in small nanostructures.

Irradiation reduction (S K Mahapatra, K A Bogle, S D Dhole and V N Bhoraskar, Nanotechnology 18 (2007) 135602). Electron irradiation (electron energy) is a new method of reduction of precursor in a solution to produce nanoparticles.

Microemulsion method (Zhi Ya Ma, Dosi Dosev and Ian M Kennedy, Nanotechnology 20 (2009) 085608). Microemulsion consists of a ternary mixture of water, surfactant and oil or a quaternary mixture of water, surfactant, co-surfactant and oil. Different surfactant, that is, different microemulsion system employed in the fabrication process, silver nanoparticles with different diameters or morphologies are obtained.

Biochemical reduction (M. Sathishkumar, K. Sneha, S. W. Won, C. W. Cho, S. Kim, Y. S. Yun, Colloids and Surfaces B: Biointerfaces 73 (2009) 332-338; K. Kalishwaralal, V. Deepak, S. R. K. Pandian, M. Kottaisamy, S. Barath Mani-Kanth, B. Kartikeyan, S. Gurunathan, Colloids and Surfaces B: Biointerfaces 77 (2010) 257-262), and so on.

The top-down techniques use silver metal in its bulk form, then, mechanically reduce its size to the nanoscale via specialized methodologies such as lithography (Xiaoyu Zhang, Alyson V. Whitney, Jing Zhao, Erin M. Hicks, and Richard P. Van Duyne, Journal of Nanoscience and Nanotechnology Vol. 6, 1-15, 2006,) and laser ablation (A. Pyatenko, K. Shimokawa, M. Yamaguchi, O. Nishimura, M. Suzuki Appl. Phys. A, 79, 803-806 (2004)).

Foremost among all of the above processes is the chemical reduction method that allows production of large quantities of nanoparticles in relatively short periods of time. The other processes are complex and/or require expensive controls and/or infrastructure.

It was observed that with time or high storage temperature, the particles tend to grow or aggregate to form large particles. Coalescence of the nanoparticles may lose their characteristic properties. Thus, stability of the nanoparticles in dispersion is a matter of concern for long time use and to achieve the same efficacy. Antonio M. Brito-Silva et. al., Journal of Nanomaterials, 2010, Article ID 142897, reported synthesis of silver nanoparticles by laser ablation in preformed colloids in non-aqueous media of methanol, acetone, ethylene glycol etc. The stability could be achieved from 8 days till a maximum of around 5 months with different protective agents in non-aqueous media. Some have tried to see the effect of different protective agents on aggregation behaviour of silver nanoparticles and its antimicrobial activity (L Kvitek, A Panacek and J Soukupova, J. Phys. Chem. C 112 5825 (2008); J Soukupova, L Kvitek et al., J Materials Chemistry and Physics 111 77 (2008)). It was observed that addition of ionic protective agents improved the zeta potential (stability) of the nanoparticle dispersion than without protective agents. However, the use of ionic surfactants, which gave the best results, could improve the stability of nanosilver dispersion to only a limited period and antimicrobial activity (MIC value) to 1 ppm.

The antimicrobial activity of silver nanoparticles may be evaluated either in dispersion form to give MBC/MIC values in ppm (µg/ml of dispersion) or after application on substrates in % reduction of microbial growth for a given concentration of silver in ppm (µg/g of fabric) using standard methods such as AATCC100, ASTM E 2149.

The literature reports Minimum Bactericidal Concentration (MBC) for dispersions of silver nanoparticles against pathogenic bacteria to human is in the range of 2-100 ppm for spherical shape. One of the prior art showed 6.7 ppm of 25-50 nm silver nanoparticles against S. aureus and 2 ppm against s. epidermidis using reducing agent saccharides maltose (Ales Panacek, Libor Kvitek, Robert Prucek, Milan Kolar, Renata Vecerova, Nadezda Pizurova, Virender K. Sharma, Tatjana Nevecna, and Radek Zboril, J. Phys. Chem. B 2006, 110, 16248-16253). Another prior art reported an average particle size of 18 nm of spherical nanosilver and MBC values in the range from 10 to 0.15 µg/ml (ppm) against various bacteria that are pathogenic to lower animals such as fish. However, the MBC values were evaluated after 30-90 minutes of incubation time, which is a very short time to see the actual growth of pathogen and is not a standard procedure to evaluate MBC. (Soltani, M., Ghodratnema, M., Ahari, H., Ebrahimzadeh Mousavi, H. A., Atee, M., Dastmalchi, F., Rahmanya, J., Int. J. Vet. Res. 3, 2:137-142, 2009). In another paper, (Ansari M A, Khan H M, Khan A A, Malik A, Sultan A, Shahid M, Shujatullah F, Azam A, Biology and Medicine, Vol 3 (2) Special Issue: 141-146, 2011).

In another paper, (Ansari M A, Khan H M, Khan A A, Malik A, Sultan A, Shahid M, Shujatullah F, Azam A, Biology and Medicine, Vol 3 (2) Special Issue: 141-146, 2011) MBC value of 12.5 to 100 µg/ml (ppm) have been reported towards *Staphylococcus aureus*, methicillin-sensitive *S. aureus* (MSSA), and methicillin-resistant *S. aureus* (MRSA) were examined against commercially available nanosilver particles (5-10 nm particle size).

Sukdeb Pal et. al. (Sukdeb Pal, Yu Kyung Tak, 5 Joon Myong Song, Appl. Environ. Microbiol, 2007 March; 73(6): 1712-1720) have done comparative study on bactericidal properties of different shaped silver nanoparticles with *E. Coli*. They have shown MIC value for truncated triangular silver nanoparticle to be 1 µg (or 1 ppm), for spherical 50-100 µg (or 50-100 ppm) and for rod shaped particles >100 µg (or >100 ppm).

Antimicrobial activity of silver nanoparticles on textile substrates have also been reported in several studies. For effective antimicrobial activity (>80%) on textile substrates, finishes based on silver nanoparticles are applied on textiles/substrates in concentrations from 5 ppm (Hee Yeon Ki, Jong Hoon Kim, Soon Chul Kwon, Sung Hoon Jeong, J Mater Sci (2007) 42:8020-8024) to 350 ppm (Kanokwan Saengkiettiyut, Pranee Rattanawaleedirojn and Supin Sangsuk, J. Nat. Sci. Special Issue on Nanotechnology (2008) Vol. 7(1)), 75), and even as high as 1000 ppm (Kanokwan Saengkiettiyut, Pranee Rattanawaleedirojn and Supin Sangsuk, J. Nat Sci. Special Issue on Nanotechnology 7 75 (2008).

The silver is a precious metal and its application at higher concentration is commercially undesirable. The result of such a high concentration application eventually gives the fabric yellow to brown tinge depending on concentration. Durability of the silver nanoparticle finish is also a concern. Silver nanoparticles tend to wash off during repeated washing. And if the Ag nanoparticles are used with binders, though wash durability improves to some extent, the maximum efficiency/antimicrobial activity of nanoparticles gets reduced due to hindrance of binder.

In order to overcome the yellowing nature of dispersion of nanosilver, when applied as finish on textile fabrics, nanosilver dispersion of colours other than yellow and brown such as blue or purple can be prepared using the knowledge available in prior art. This can be done either in a solvent (non aqueous) or water (aqueous) system. Most of the processes for different coloured silver dispersions have been prepared in non-aqueous media, which is toxic, not ecofriendly, expensive, and inappropriate for application on variety of substrates such as textile, sport goods, biomedical material, etc.

Only a few studies have been successful in producing such coloured nanosilver dispersion using aqueous system. These often involve preparation by light irradiation reduction method, which is a slow process (Shih-Hong Ciou, Yi-Wei Cao, Huai-Cing Huang, De-Yan Su, and Cheng-Liang Huang, J. Phys. Chem. C 2009, 113, 9520-9525; Lakshminarayana Polavarapu, Qing-Hua Xu, Mohan S. Dhoni and Wei Ji, APPLIED PHYSICS LETTERS 92, 263110, 2008; Jing An, Bin Tang, Xianliang Zheng, Ji Zhou, Fengxia Dong, Shuping Xu, Ye Wang, Bing Zhao, and Weiqing Xu, J. Phys. Chem. C 2008, 112, 15176-15182) gives silver nanodispersions with mixtures of different shape and size particles and three main plasmonic peak were observed at 331, 482 and 661 nm (Bin Tang, Shuping Xu, Jing An, Bing Zhao, and Weiqing Xu, J. Phys. Chem. C 2009, 113, 7025-7030) with low stability of 2-3 months (Bin Tang, Jing An, Xianliang Zheng, Shuping Xu, Dongmei Li, Ji Zhou, Bing Zhao, and Weiqing Xu, *J. Phys. Chem. C* 2008, 112, 18361-18367) under normal environmental condition. In aqueous based systems, when reduction is done via chemical reduction technique, mainly bigger triangular nanoparticle in the range of 35-200 nm mixed with other shaped particles (Isao Washio, Yujie Xiong, Yadong Yin, and Younan Xia, Adv. Mater. 2006, 18, 1745-1749; Xiaomu Wu, Peter L. Redmond, Haitao Liu, Yihui Chen, Michael Steigerwald, and Louis Brus, J. AM. CHEM. SOC. 9 VOL. 130, NO. 29, 2008; Sihai Chen and David L. Carroll, Mat. Res. Soc. Symp. Proc. Vol. 775, 2003).) has been observed.

Document "Rapid thermal Synthesis of Silver nanoprisms with Chemically Tailorable Thickness", Advanced Materials, 17, No. 4, Feb. 23, 2005, By Gabriella S. Métraux and Chad A. Mirkin discloses Silver Nanoprisms prepared by a thermal synthetic route resulting in silver nanoprisms with unimodal size distribution. The final colour of the colloidal solution ranged from pink/purple to Turquoise depending on the concentration of $NaBH_4$ used. However, the blue colour colloids were mixture of both prisms (triangular) and spherical shaped particles because the prisms were grown starting from yellow spherical particles as in irradiation method. UV spectrum of blue coloured colloids had three peaks related to the Plasmon bands created with triangular prisms. Also the particle size of silver nanoparticles was large in the range of 20 nm to 50 nm. Though antimicrobial activity of these colloids were not reported, based on other studies as reported above, it is likely that these colloids would be needed to be applied in large concentrations for effective antimicrobial activity due to their large particles size. The dispersion of nanosilver prepared in this prior art was also light sensitive and was stable for only a few months when stored in dark.

Thus, there arises a need to develop antimicrobial finishes based on nano silver that have higher stability, wash durability, antimicrobial activity, and also, that act as a brightening/bluing agent for retaining whiteness of or brightening the white and pale coloured substrates.

The present invention solves the problems of yellowing of fabric and other substrates on application of nanosilver finishes, stability of the aqueous dispersion of nanosilver during storage, their application at low concentrations, and wash durability of nanosilver finish on application. The aqueous dispersion of silver nanoparticles of the present invention is blue in colour, has nanosilver particles of very small in size, and can combine the effect of antimicrobial finish and brightening/bluing agent used for brightening the white and pale coloured substrates. It shows 99.99% antimicrobial activity at very low concentrations, is easy to synthesize directly in aqueous media, and is stable on storage even at high temperature and/or in light. The dispersion stability of the nano silver particles of present invention is for 15 to 24 months. The particles provide wash durability after application on textile, binding with simple heat treatment at temperatures greater than 120 degree C. (120 to 150 degree C.) or with binders at room temperature. The particles and their dispersions have very high compatibility with binders and surfactants of various types.

OBJECTIVES OF THE INVENTION

An objective of the present invention is to provide blue coloured aqueous dispersion of silver nanoparticles characterized with plasmonic peaks in the range 330-335 nm and 650-720 nm combined with missing plasmonic peaks in the range 390 to 410 nm and 410-500 nm in UV-Vis spectrum and with high molar extinction coefficient in the range of 10.1 to 15.7 mM$^{-1}$ cm$^{-1}$ at wavelength of maximum absorption in the range 650-720 nm.

Another object of the present invention is to provide a process for preparation of blue colored aqueous dispersion of silver nanoparticles directly from precursors in one step.

Yet another object of the present invention is to provide composition comprising blue colored aqueous dispersion of silver nanoparticles of the present invention for use as anti microbial agents or finishes.

In yet another object of the present invention, the blue colored aqueous dispersion of the silver nanoparticles has majority of silver particles in the range of 0.5 nm to 6 nm (in equivalent diameter term) and suitable as antimicrobial finish and optical brightening/bluing agent used for brightening the white and pale coloured substrates and is stable on exposure to light and/or to high temperature.

SUMMARY OF INVENTION

The present invention provides blue colored aqueous dispersion of silver nanoparticles which is very stable and very effective antimicrobial agent having characteristic feature of having plasmonic peaks in the range 330-335 nm and 650-720 nm combined with missing plasmonic peaks in the range 390 to 410 nm and 410-500 nm in UV-Vis spectrum, having high molar extinction coefficient in the range of 10.1 to 15.7 mM$^{-1}$ cm$^{-1}$ at wavelength of maximum absorption in the range 650-720 nm, the dispersion having silver nanoparticles of anisotropic shape with majority of particles (>65) having equivalent diameter in range of 0.5 to 6 nm and Minimum Bactericidal Concentration (MBC) lower than 0.10 ppm preferably in the range of 0.055-0.099 ppm.

In an embodiment, the present invention also provides process for preparation of said aqueous dispersion.

The process of the present invention comprises steps of adding a protecting agent to silver precursor solution, followed by addition of stabilizer and hydrogen peroxide. The temperature is raised followed by addition of a reducing agent, which leads to formation of blue coloured aqueous dispersion of silver nanoparticles directly from precursor.

In an embodiment present invention provides compositions comprising blue coloured aqueous dispersion of silver nanoparticles produced by the method of present invention.

LIST OF DEFINITIONS

Molar extinction coefficient (c): It is the measure of how strongly a substance absorbs light at a particular wavelength. It is given by $\epsilon=A/cL$, where A is absorption record in a UV-vis, c is concentration of dispersion in mMoles and L is pathlength of the sample measuring cell.

Antimicrobial activity: Percentage reduction of microbes of an antimicrobial agent at a particular concentration. It can be evaluated by different standard testing methods either qualitatively or quantitatively. For non leaching type of testing more preferred method is colony counting method e. g. AATCC 100, ASTM E-2149. For leaching type of testing more preferred method is zone of inhibition e.g. AATCC 47, AATCC 90 etc.

Minimum Bactericidal concentration (MBC): It is the lowest concentration of antimicrobial agent required to kill the germ.

Procedure to evaluate MBC of aqueous dispersion of Blue Ag nanoparticle: It is done by AATCC 100 (colony counting method). The silver dispersions were diluted 50-1000 times with Luria broth solution, inoculated with the tested bacteria at a concentration of $10^5$ to $10^6$ CFU/mL. The minimum bactericidal concentration (MBC) was evaluated after 24 h of incubation at 37° C. After 24 hours of incubation, the minimum particular Ag concentration was determined at which more than or equal to 99.9% bacteria were killed.

Protective agent/stabilizer: It is a material that prevents the nanoparticles in aggregating in dispersion (liquid media).

Zeta Potential: It is the potential difference between the dispersion medium (here water) and the stationary layer of fluid attached to the dispersed particle. It indicates the degree of repulsion between adjacent, similarly charged particles in a dispersion. Its units are mV.

Stability: Stability of a dispersion is related to the time taken by the dispersed particles in a dispersing medium to agglomerate and settle down under gravity. This makes the dispersion inhomogeneous and can not be used for applications. Dispersion with higher stability takes longer time to settle down.

Dynamic light scattering (DLS): It sometimes referred to as Photon Correlation Spectroscopy (PCS) or Quasi-Elastic Light Scattering (QELS), is a well-established technique for measuring the size of macromolecules and particles typically in the submicron region. Particles, emulsions and macromolecules in suspension undergo Brownian motion. This is the motion induced by the bombardment by solvent molecules that themselves are moving due to their thermal energy. If the particles or molecules are illuminated with a laser, the intensity of the scattered light fluctuates at a rate that is dependent upon the size of the particles. Analysis of these intensity fluctuations yields the velocity of the Brownian motion and hence the particle size using the Stokes-Einstein relationship (Malvern Instruments, technical note). The fundamental size distribution generated by DLS is an intensity distribution, and then, it is converted, using Mie theory (Malvern Instruments, technical note; Chem. Rev. 2007, 107, 4797-4862), to a volume distribution. Intensity graph is not a true representation of amount of particles, as scattering intensity of signal is proportional to diameter of particle.

Hydrodynamic diameter: It is the composite diameter of a particle (surrounded by different ions and protective agents) in liquid media. In general, true diameter of the particle is less than its hydrodynamic diameter.

Washing using method AATCC-61-IIA:

Temperature used: 49 degree C., Time: 45 minutes, Steel ball: 50 steel balls, Soap used: Non-ionic detergent (0.15 wt %). This washing technique simulates actual conditions equivalent to 5 home laundry washings.

DETAILED DESCRIPTION

Blue coloured dispersion of silver nanoparticles is generally composed of truncated triangular or triangular nanoplates, which have active facets (111). It is believed that high-atom-density facets such as {111} favor the reactivity of silver and it is having direct interaction with the bacterial surface.

Thus, blue coloured aqueous dispersion of silver nanoparticles having higher reactivity, in comparison to other blue coloured particles/dispersions reported in the literature, has been developed using a new method of preparation and using different concentration of additives. This blue coloured aqueous dispersion of Ag nanoparticles has overcome the above-mentioned shortcomings of the antimicrobial nanofinishes based on prior art. The combination of characteristic features of the Blue coloured dispersion of silver nanoparticles of the present invention, which distinguishes it from the prior art, are (a) the smaller size of the silver particle (measured by Small angle X-ray Scattering (SAXS) to be less than 6 nm in diameter for majority (i.e. 65% to 95%) of the particles (diameter range varies from 0.5 to 6 nm, peak value 2.6 nm for more than 70% particles) (b) Ag particles of a unique anisotropic shape as evidenced by appearance of plasmonic peaks in the range 330-335 nm and 650-720 nm combined with absence of plasmonic peaks in the regions of 390-410 nm (seen for isotropic spherical particle) and 410-500 nm seen for triangular shaped particles reported in the prior art (c) molar extinction coefficient greater than 10 $mM^{-1}$ $cm^{-1}$ (in the range of 10.1-15.7 $mM^{-1}$ $cm^{-1}$) at wavelength of maximum absorption, which occurs in the range of 650-720 nm, (d) Minimum Bactericidal Concentration (MBC) lower than 0.10 ppm (in the range of 0.055-0.099 ppm), (e) dispersion stability greater than 15 months (in the range of 15-24 months), and (f) optical brightening effect, which does not allow yellowing of cotton fabrics of different constructions (woven, knits, towel etc.) when applied at 0.1-8 μg/g and dried at 120 deg C. and imparts improved brightness at same concentrations when drying condition is kept below 100 deg C.

The coloured dispersion of Ag nanoparticles obtained by the process of the present invention is optionally mixed with surfactants and binders to yield even more effective compositions for antimicrobial finishing of textiles as evidenced by increase in molar extinction coefficient in the range of 14.1-19.0 $mM^{-1}$ $cm^{-1}$ and minimum bactericidal concentration (MBC) values lower than 0.09 ppm, more preferably in the range (0.055 to 0.01 ppm), for control of the growth of microbes and perspiration odors for a variety of substrates including textile materials such as cellulosics such as cotton, wool, silk, polyester, viscose, polypropylene, nylons, Lycra, acrylic etc, and blends thereof.

Blue coloured aqueous dispersion of silver nanoparticles of present invention can be applied during textiles manufacture, processing, finishing and printing of various forms of fibers, filaments, yarns, sewing threads, towels, knits & woven & non woven textile and apparel.

Blue coloured aqueous dispersion of silver nanoparticles described in the present invention can be applied along with durable press and wrinkle free finishing systems. The wrinkle free systems include thermosetting resins such as dimethylol dihydroxy ethylene urea (DMDHEU) resins; Dimethyl dihydroxy ethylene urea (DMeDHEU) certain transition-metal complexes, along with catalysts used for resin curing, polyethylene emulsions, softeners etc. This cross linking of blue silver with resin system provides durability on apparel up to 50 washes at an application dosage level of 2% of the fabric weight.

Blue coloured aqueous dispersion of silver nanoparticles described in the present invention also finds antimicrobial applications in many different textiles for the home, apparel, medical, military and industrial use. Non-limiting examples of such textiles are shape-wear, socks, mattress ticking, roller hand towels, dish towels, bed linen, upholstery, soft furnishings, curtains, boot and shoe linings, carpets and mats, innerwear, intimate apparel and underwear briefs, T-shirts, active and athletic wear, leisure wear, sleepwear, swimwear, suits, uniform fabric & work wear, knitwear, denims, trousers, women's' knee-highs, hosiery and leg wear.

Blue coloured aqueous dispersion of silver nanoparticles described in the present invention can be incorporated into articles of clothing for antimicrobial applications in jackets, vests, headwear, footwear (toe caps, heels, insoles, uppers, etc.), gloves, scarves, socks and leggings, neck gaiters, tents, sheeting & bedding, coated fabrics (PV, Polyurethanes, Silicone & PVC), sportswear, bath rugs, luggage fabrics, sleeping bags & duvets, and hats.

Blue coloured aqueous dispersion of silver nanoparticles described in the present invention is compatible for use along with textile processing chemicals and chemical auxiliaries. Textile auxiliaries include but are not limited to textile finishing agents, fabric conditioners, moisture management finishes, antistatic agents, nucleating agents, soil release agents, optical brightening agents, antioxidants, UV stabilizers, fillers, softeners, lubricants, curing accelerators, encapsulated fragrances, textile detergents, and the like for providing malodor control and antimicrobial properties. All of such additional materials are well known to those skilled in the art and are commercially available.

Blue coloured aqueous dispersion of silver nanoparticles described in the present invention can be used in textile composite materials including but not limited to textile foot mattress composites. Textile accessories including but not limited to textile collar linings, shirt buttons jacket fiber fillers and jacket insulating materials. All of these benefit from the antimicrobial protection provided by Blue colored silver nanoparticles as described in the present invention.

Blue coloured aqueous dispersion of silver nanoparticles described in the present invention can be used for textile recycling and waste recycling to avoid the malodor generated during recycling and to help avoid the spread of diseases which may arise during the recycling process. Blue colored aqueous dispersion of silver nanoparticles described in the present invention can be used in textile preservation, including protection from dampness of apparel in all textile fabrics including canvass fabrics. Aqueous dispersion of blue coloured silver nanoparticles described in the present invention can be incorporated into non-woven fabrics and usually added along with latex binders for various applications including but not limited to non woven air filters.

Blue coloured aqueous dispersion of silver nanoparticles described in the present invention can be incorporated into a wide range of consumer goods products, for the purpose of bringing an additional antimicrobial effect, or a boosted freshness effect. Examples of such products include but are not limited to washing detergents, whether in liquid, powder, tablet or gel form, or rinse conditioners or rinse additives whether dilute or concentrate in nature. Also included are laundry wash additives such as stain removal enhancement products. Blue colored aqueous dispersion of silver nanoparticles can also be incorporated into tumble drier sheets. Additionally, blue colored aqueous dispersion of silver nanoparticles can be incorporated into fabric sprays, both with and without additional fragrance.

Blue coloured aqueous dispersion of silver nanoparticles described in the present invention can be incorporated into many household products to bring an additional antimicrobial benefit or a freshness enhancement. This includes but is not limited to cat litter, air fresheners, hard surface cleaners and sprays, and floor cleaners. Blue Silver can also be used to treat mops, wipes and cloths to prevent bacterial growth and to keep such substrates fresh.

Blue coloured aqueous dispersion of silver nanoparticles described in the present invention can be used to enhance the antimicrobial properties of a broad range of paper based products, such as diapers, incontinence products, facial tissues, toilet tissues, wipes and kitchen towels.

Blue coloured aqueous dispersion of silver nanoparticles described in the present invention can be incorporated into numerous personal care products, including but not limited to such products as deodorants, anti-perspirants, talcum powders, body lotions, hair shampoos, hair conditioners, shower gels, bar soaps, body lotions and moisturizers and shaving gels.

Blue coloured aqueous dispersion of silver nanoparticles described in the present invention can be incorporated into air filters, which can be vehicle and aircraft cabin air filters, or room and building based air filters in homes, offices and hotels. Blue colored aqueous dispersion of silver nanoparticles incorporation ensures filter materials are resistant to bacterial and fungal growth.

Blue coloured aqueous dispersion of silver nanoparticles described in the present invention can be incorporated into medical dressings such as wound care materials and burn dressings to suppress bacterial and fungal growth, and the related risk of infection, in materials used for wound care dressings and burn dressings. In addition, blue colored aqueous dispersion of silver nanoparticles can be utilized in medical-healthcare products such as medical/healthcare wipes possessing anti-microbial properties.

An additional use for blue coloured aqueous dispersion of silver nanoparticles as described in the present invention is in paints, coatings and wood preservative products, where it acts as a preservative and also delivers antimicrobial properties to the products.

Blue coloured aqueous dispersion of silver nanoparticles described in the present invention can be incorporated into products designed to repel or eradicate bedbugs, such as textile coverings and sprays. The textile coverings include but are not limited to mattress ticking, sheets and bed coverings, and mattress coverings.

Blue coloured aqueous dispersion of silver nanoparticles described in the present invention can be incorporated into products designed to kill or repel lice. This can be incorporated into textiles, covering and sprays or gels. Non-limiting examples are hats, hair netting and caps, hair spray, hair gels and creams.

Blue coloured aqueous dispersion of silver nanoparticles of present invention can provide residual protection against pests like microorganisms or insects, growth of bacteria and can kill existing bacteria on various surfaces.

Blue coloured aqueous dispersion of silver nanoparticles of present invention is effective against formation of Bio films on various surfaces.

The present invention provides blue colored aqueous dispersion of silver nanoparticles which is very stable and very effective antimicrobial agent having characteristic feature of having plasmonic peaks in the range 330-335 nm and 650-720 nm combined with missing plasmonic peaks in the range 390 to 410 nm and 410-500 nm in UV-Vis spectrum, having high molar extinction coefficient in the range of 10.1 to 15.7 mM$^{-1}$ cm$^{-1}$ at wavelength of maximum absorption in the range 650-720 nm, the dispersion having silver nanoparticles of anisotropic shape with majority of particles ((65-95%)) having equivalent diameter in range of 0.5 to 6 nm (peak value 2.6 nm of more than 70%) and Minimum Bactericidal Concentration (MBC) lower than 0.10 ppm preferably in the range of 0.055-0.099 ppm.

The present invention also provides a process for preparation of blue coloured aqueous dispersion of silver nanoparticles, the process comprising the steps of
 (i) adding a protecting agent to a silver precursor solution;
 (ii) adding a stabilizer and hydrogen peroxide to the solution of step (i);
 (iii) heating solution of step (ii) to a temperature in the range of 50 to 90 degree C.; and
 (iv) reducing the solution of step (iii) with a reducing agent to obtain blue coloured aqueous dispersion of silver nanoparticles.

The present invention also provides compositions comprising blue coloured aqueous dispersion of silver nanoparticles for various applications described above.

In an embodiment, the silver precursor is selected from a group consisting of silver nitrate, silver perchlorate, silver acetate, silver sulphate and silvertetraoxychlorate.

In an embodiment, the silver precursor is silver nitrate.

In another embodiment, the protecting agent is selected from a group consisting of poly(ethylenediamine), sodium acetate, bis(p-sulfonatophenyl)phenyl phosphine dipotassium dihydrate, polythene glycol, polyvinyl alcohol and polyvinyl pyrrolidone.

In another embodiment, the protecting agent is polyvinyl pyrrolidone.

In yet another embodiment, a stabilizer is selected from the group consisting of ethylenediamine tetra acetate salt, nitrilo acetic acid salt and trisodium citrate.

In yet another embodiment, a stabilizer is trisodium citrate.

In another embodiment, a surfactant is optionally added before step (iv).

In still another embodiment, the surfactant is selected from the group consisting of anionic and non ionic surfactants including sodium dodecyl sulfate (SDS), polysorbates, sodium salts of polyacrylic acids, ethylenediamine tetra acetate salt, nitriloacetic acid salt and trisodium citrate and condensates of benzo sulphonic acids.

In still another embodiment, the surfactant is sodium dodecyl sulfate (SDS).

In yet another embodiment, the reducing agent is selected from the group consisting of ascorbic acid, sodium tri-sec-butylborohydrate, lithium aluminium hydride, potassium tri-sec-butyl borohydride, potassium triethylborohydride, sodium triacetoxy borohydride and sodium borohydride.

In yet another embodiment, the reducing agent is sodium borohydride.

In yet another embodiment, the reaction mixture is heated in the range of 50 to 90° C. preferably in the range of 60-65° C.

In yet another embodiment, the mole ratio of silver precursor to protective agent is in the range of 1:0.1 to 1:100, preferably 1:1 to 1:10, more preferably 1:1 to 1:5.

In still another embodiment, the mole ratio of silver precursor to stabilizer ranges from 1:1 to 1:100, preferably 1:1 to 1:50, more preferably 1:5 to 1:15.

In yet another embodiment, the mole ratio of silver precursor to reducing agent is in the range of 1:8.5 to 1:50 preferably 1:10 to 1:20.

In yet another embodiment, the mole ratio of silver precursor to hydrogen peroxide is in the range of 1:50 to 1:500, preferably 1:100 to 1:300.

In yet another embodiment, wherein the mole ratio of silver precursor to surfactant is in the range of 1:0.5 to 1:350, preferably in the range of 1:5 to 1:50 of the mixture.

The blue coloured aqueous dispersion of Ag nanoparticles obtained by the process of present invention is optionally mixed with surfactants and binders to yield effective compositions for antimicrobial finish for variety of substrates including textile material such as cellulosic, wool, silk, polyester and nylons etc.

In still another embodiment, a composition made in water comprising 1-99 wt % of blue coloured aqueous dispersion of silver nanoparticles, 0.001 to 10 wt % preferably 0.01 to 1.0 wt % of a surfactant optionally with 0.1 to 10 wt % of a binder of the final composition.

In still another embodiment, a composition made in water comprising 1-99 wt % of blue coloured aqueous dispersion of silver nanoparticles with a binder in the range of 0.1 to 10 weight % of the final composition.

In still another embodiment, the surfactant is selected from the group consisting of anionic and non ionic surfactants including sodium dodecyl sulfate (SDS), polysorbates, sodium salts of polyacrylic acids, and condensates of benzo sulphonic acids or a mixture of any two or more selected from the group.

In still another embodiment, the surfactant is sodium dodecyl sulfate (SDS).

In still another embodiment, the binder is selected from the group consisting of acrylic based binder, epichlorohydrin-bishexamethylenetriamine based binder, copolymer binder with maleic acid, epoxy based binders, polyurethane based, and polyester based resin binders.

In still another embodiment, the binder is epichlorohydrin-bishexamethylenetriamine based binder.

In yet another embodiment, the minimum bacteriocidal concentration (MBC) of the composition is lower than 0.09 ppm (range 0.055 ppm to 0.01 ppm).

In still another embodiment, the molar extinction coefficient of the composition is above 14 $(mM-cm)^{-1}$, preferably in the range 14.1-19.0 $(mM-cm)^{-1}$.

In still another embodiment, the compositions gives no yellowing effect when applied on cotton fabrics at 120 deg C.-150 deg C. and gives whiteness index higher than the control fabric by 10-85% when applied on fabric at 30-100 deg C.

The process of the present invention provides blue coloured aqueous dispersion of silver nanoparticles with quantitative yield, smaller size, better purity with respect to particle shape and size, absence of plasmonic bands in the wavelength range of 390-500 nm and high molar extinction coefficient with significantly better properties, such as higher stability to exposure to light and heat, higher dispersion stability with storage time, and better compatibility with various additives, higher antimicrobial activity at lower concentrations and higher fixation to polymeric substrates as compared to the processes and products of the prior art.

The present invention also provides composition of blue coloured aqueous dispersion of silver nanoparticles. In a preferred embodiment the aqueous composition comprises the blue coloured aqueous dispersions of silver nanoparticles as obtained above with a surfactant optionally with a binder, which gives even higher molar extinction coefficient, better dispersion stability, higher antimicrobial activity and higher fixation on substrate than the above mentioned composition without surfactant.

The amount of blue coloured aqueous dispersion of silver nanoparticles in the composition may vary in the range of 1-99 wt %, surfactants in the composition may vary in the range from 0.001 to 10 weight %, preferably 0.01 to 1 wt % and binder in the range 0.1 wt % to 10 wt %. of the final composition.

Example 1

Synthesis of Aqueous Dispersion of Blue Coloured Silver Nanoparticles

In 100 ml of deionized water, 0.01 mMole of $AgNO_3$ was added. To this, 0.035 mMole of Poly(vinyl pyrrolidone) of number average molecular weight of 40,000 was mixed. Then 0.092 mMole of trisodium citrate and 2.0 mMole of $H_2O_2$ were added stepwise and mixed at the room temperature at 20° C. Then the temperature of the mixture was raised to 65° C. and then 0.184 mMoles of sodium borohydride was added to produce blue coloured aqueous dispersion of Ag nanoparticles.

Example 2

In 100 ml of deionized water, 0.01 mMole of $AgNO_3$ was taken in a beaker. 0.05 mMole of Poly(vinyl pyrrolidone) of number average molecular weight of 40,000 was mixed with it. Trisodium citrate (0.090 mMole) and $H_2O_2$ (2.0 mMole) were added stepwise and mixed at the room temperature at 40° C. Then the temperature of the mixture was raised to 60° C. and then 0.15 mMole of sodium borohydride was added to produce blue coloured aqueous dispersion of Ag nanoparticles.

Example 3

Application of Blue Coloured Aqueous Dispersion of Silver Nanodispersion on Textile Substrate 1 wt % of blue coloured aqueous dispersion produced in Example 1 was taken in DI water. To this 0.1 wt % SDS was added and stirred well. Fabric dipped and padded with 80-100% expression (% weight of liquid based on the dry weight of fabric). Fabric was dried at 80 degree C. for 5 min and cured at 150 degree C. for 3 min to get durable antimicrobial finish with out binder.

Example 4

A Composition of the Blue Coloured Aqueous Dispersion of Silver Nanodispersion 1 wt % of blue coloured aqueous dispersion produced in Example 1 was taken in water. To this 0.5 wt % of SDS was added and mixed well. To this 1 wt % of Epichlorohydrin-bishexamethylenetriamine polymer based binder was added and mixed well by stirring at room temperature.

Example 5

The Fabric was dipped and padded using the mixture of Example 4 at an expression of 80-100%. The treated fabric was dried at room temperature to get durable antimicrobial finish.

Product Properties of Blue Coloured Aqueous Dispersion of Silver Nanoparticles.

Figure 1:
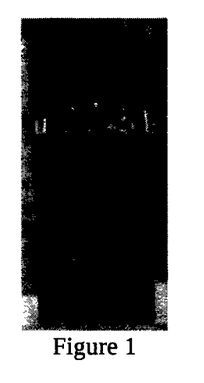
FIG. 1: Optical photograph of blue coloured aqueous dispersion of silver nanoparticles.
Figure 2:
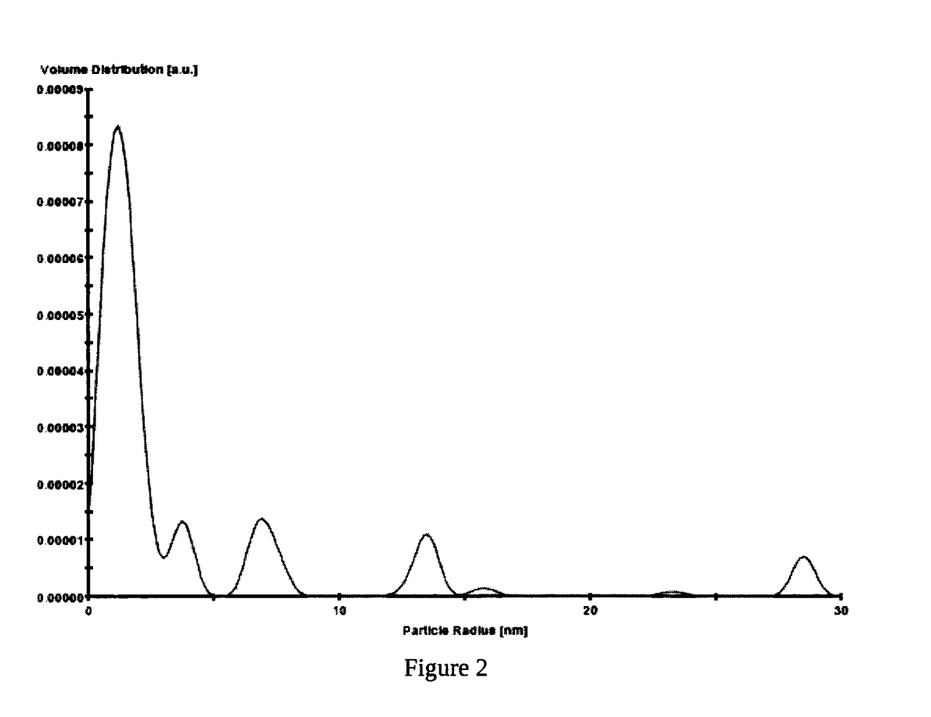
FIG. 2: Small Angle X-ray Diffraction (SAXS) graph of blue coloured aqueous dispersion of silver nanoparticles showing distribution of particle size by volume. SAXS shows actual size of the majority Ag particles to be less than 6 nm (equivalent diameter range varies from 0.5 to 6 nm, peak value occurs at 2.6 nm for more than 80% particles). Higher sizes are in minority and are likely to be agglomerates of smaller particles.

A. Size and Shape of the Aqueous Dispersion of Blue Coloured Silver Nanoparticles 1. Small Angle X-Ray Diffraction Measurement for Precise Particle Size Analysis The size of blue coloured aqueous dispersion of silver nanoparticles determined by small angle x-ray diffraction is shown in FIG. 2. The data has been converted to volume size clearly shows that the majority of the nanoparticles are of size <6 nm (2.6 nm for more than 70%, 7.6 nm 4-5%, 12.4 nm 4-5%).

2. UV Absorption Spectroscopy Analysis

Figure 3:
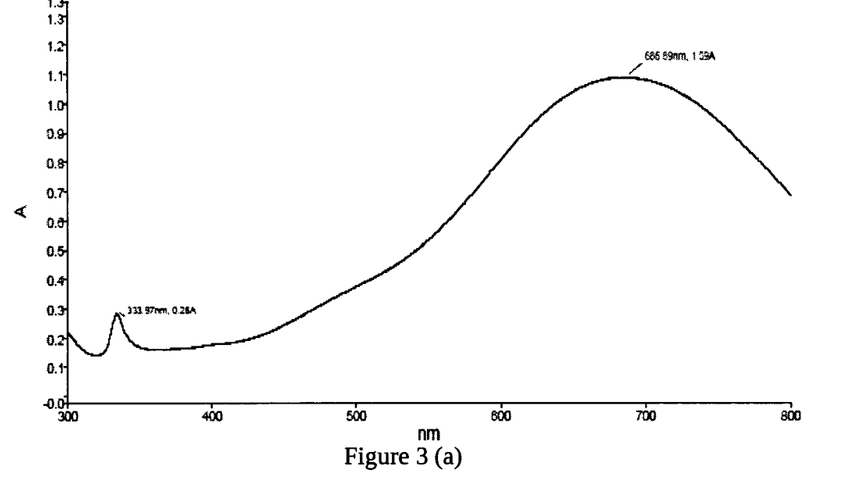
FIG. 3: UV-vis spectrum of blue coloured aqueous dispersion of silver nanoparticles prepared in Example 1(a) as prepared and (b) after 15 months. The graph shows stability of dispersion for over 15 months.

The UV-Vis measurement of the as-prepared blue coloured aqueous dispersion of silver nanoparticles (FIG. 3(*a*)) gives a characteristic UV vis spectrum which clearly reflects their anisotropic shape. A major peak appears at 687 nm, & a very small peak at around 335 nm. Molar extinction coefficient of blue coloured nanosilver dispersion without surfactant is 10.9 $(mM-cm)^{-1}$ at the maximum wavelength of absorption of 687 nm. No plasmonic peak is observed in the range 390-410 nm indicating absence of spherical silver nanoparticles. Also, there is no plasmonic peak between 410-500 nm indicating a substantially different shape and/or size than those reported for prisms of prior art. The mathematical modeling of the nanoparticles has shown that occurrence of plasmonic peaks is highly associated with the shape and size of the nanoparticles (ref. Advanced Materials, 17, No. 4, February 23, (2005), By Gabriella S. Métraux and Chad A. Mirkin). The aqueous dispersions of silver nanoprisms of prior art show at least three and sometime four plasmonic bands in the range 300-350 nm, 390-410 nm, 410-500 nm and 650-700 nm.

The UV-Vis measurement of blue coloured aqueous dispersion of silver nanoparticles after 15 months of storage is shown in FIG. 3(*b*). The graph gives a characteristic UV-vis spectrum which clearly reflects that their anisotropic shape is preserved with time. The absence of peak in the range of 390-410 nm indicates that anisotropic particles are stable with time and have not degenerated to spherical particles. Also, the absence of peak in plasmonic band of 410-500 nm indicates that uniqueness of the silver nanoparticles is preserved with time. There is only a slight shift of maximum absorption wavelength to 714 nm is seen. The shift is likely due to the deagglomeration of bigger size particles, which is also supported by particle size analysis by DLS (see below). Molar extinction coefficient of Blue nanosilver without surfactant is 10.3 $(mM-cm)^{-1}$ at the wavelength of maximum absorption.

3. Particle Size/Zeta Analysis

Figure 4:
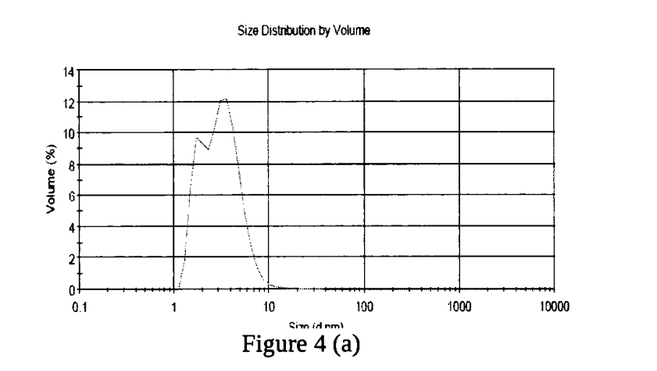
FIG. 4: Blue coloured aqueous dispersion of silver nanoparticles (after 15 months) a) Particle size distribution by volume using DLS (b) Zeta potential. DLS shows composite hydrodynamic diameter of Ag particle and the protective agent.
Figure 4B:
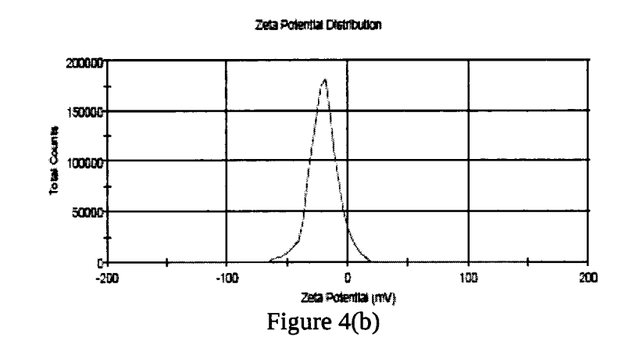

Particle size analysis of blue coloured aqueous dispersion of silver nanoparticles (FIG. 4(*a*)) (after 15 months of storage) shows particle diameter distribution by volume=2 nm, 23% and 4.13 nm, 67%, Zeta potential (FIG. 4(*b*)) is =−19.9 mV, 100%. The particle size distribution is indicating that aqueous dispersion is stable with time, which is in contrast to products of prior art. The DLS technique gives hydrodynamic diameter of composite of silver nanoparticle and the protective agent surrounding it, which is larger than the actual diameter of the particles when seen in small angle x-ray spectrometer.

4. Antimicrobial Properties

The Minimum bactericidal concentration (MBC) value for blue coloured aqueous dispersion of Ag nanoparticles is less than 0.1 ppm (in the range of 0.055-0.099 ppm) against *S. aureus* (gram positive bacteria).

5. Storage Stability of the Blue Coloured Aqueous Dispersion of Ag Nanoparticles The product is highly stable even after 15 months of storage under standard room conditions (30-40 deg C.) of tropical weather kept in normal diffused sunlight. This is supported by particle size analysis of blue coloured aqueous dispersion of silver nanoparticles at after 15 months of storage time (FIG. 4(*a*)). Particle size remains small for over 15 months.

The UV-visible spectrum of blue coloured aqueous dispersion of Ag nanoparticles remains nearly same with storage time of over 15 months under the above mentioned conditions of weather and diffused sunlight. The optical absorption has remained same, while a slight shift was seen in maximum wavelength value with storage time (FIG. 3). This implies that concentration, shape and size of Ag nanoparticles in aqueous dispersion has not changed with time. The shift is likely due to the deagglomeration of the bigger size particles to smaller agglomerates as also seen by particle size measurement.

There is also no settlement of nanosilver particles or change in colour or appearance with time. This implies that blue coloured aqueous dispersion of Ag nanoparticles is highly stable on exposure to sunlight and with storage under warm atmospheric conditions.

Figure 5:
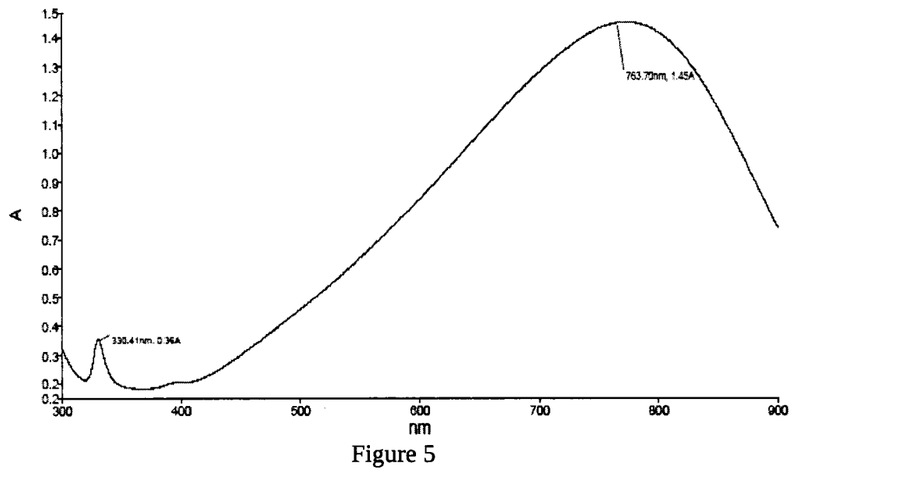
FIG. 5: UV-vis spectrum of blue coloured aqueous dispersion of silver nanoparticles with 0.1 wt % SDS surfactant.

6. Stability of Nanosilver Finish Under Different Conditions a) pH stability: The blue coloured dispersion of silver nanoparticles is stable over a wide range of pH. The pH stability range the dispersion is 7 to 14. Blue coloured aqueous dispersion of silver nanoparticles becomes purple at pH lower than 6 and eventually orange in the acidic pH of <~3.

b) Stability to sedimentation under accelerated conditions: Centrifugation at high rpm such as 6000 rpm for more for 15 minutes does not give precipitate or colour change.

c) Stability on dilution with tap water: Diluted blue coloured dispersion of silver nanoparticles (the above composition based on 0.1 mM silver, when diluted to 1 to 2%) with tap water (hardness of tap water in the range of 200 to 1000 ppm) does not give precipitate or colour change of the dispersion.

d) Compatibility with different agents and their compositions i) Compatible with non-ionic, anionic and cationic surfactants. With nonionic an dionic surfactants there is no change in the colour of the product. However, colour may shift to purple in the presence of some cationic surfactants. The compositions of blue coloured aqueous dispersions of silver nanoparticles with surfactants such as SDS (as given in Example 3) give molar extinction coefficient higher than $14.0$ $mM^{-1}$ $cm^{-1}$, more precisely, in the range of $14.1$-$19.0$ $(mM \cdot cm)^{-1}$ (FIG. 5) indicating deagglomeration of blue nanoparticles to still smaller size.

Figure 6:
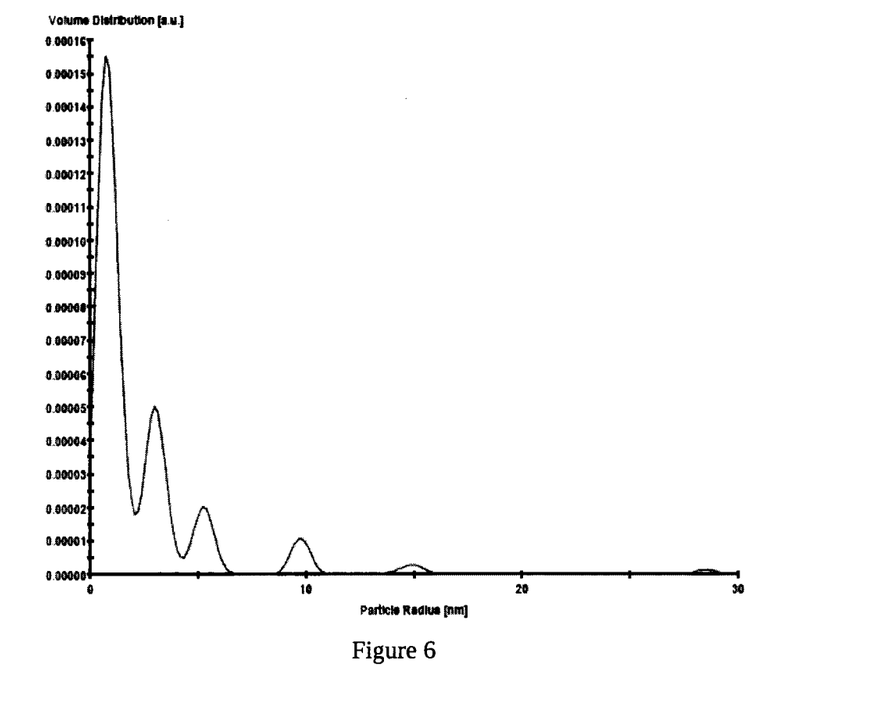
FIG. 6: Small Angle X-ray Diffraction (SAXS) graph of blue coloured aqueous dispersion of silver nanoparticles with 0.1 wt % SDS surfactant.

This is also confirmed with particle size measurement by small angle x-ray diffraction, which shows that peaks present at larger particle size values have diminished on addition of sodium dodecyl sulphate (SDS) surfactant and moved to smaller particle size values (FIG. 6). Because of de-agglomeration to smaller size, the samples show higher antimicrobial activity with MBC value of less than 0.09, more precisely, in the range 0.055 to 0.01 ppm. The higher activity and fixation of silver nanoparticles of present composition on textile fabrics is shown in Table 3.

ii) Compatibility with binders: The blue coloured aqueous dispersion of Ag nanoparticles is compatible with several types of binders and shows better properties such as higher fixation and activity on application with binders on various substrates. The types of binders tested are:

a. Acrylic based binder b. Epichlorohydrin-bishexamethylenetriamine based binder c. Copolymer binder with maleic acid d. Polyester resin, etc.

The higher activity and fixation of the composition with binders is shown in Table 3.

e) CIE Whiteness Index using Spectrophotometer (index D65 illuminate) values for cotton fabrics treated with 1% of blue coloured aqueous dispersion of silver nanoparticles of Example 1. The treatment conditions are given below:

| Application conditions | |
| --- | --- |
| Fibre Type | 100% Cotton |
| application method | padding process |
| pickup | 100% |
| pH of bath | 5.5 |
| Drying condition | 120° C. |
| Dosage | 10 grams per liter |

TABLE 1

Whiteness Index of fabrics after application of blue coloured aqueous dispersions of Example 1 at conditions mentioned in Table 2. CIE Whiteness Index using Spectrophotometer (index D65 illuminate)

| Fabric Construction | Untreated fabric | Treated with Inventive material (blue nano silver dispersion) (1% of weight of fabric; 0.1 ppm) | Treated with conventional spherical colloidal silver of particle size 5-100 nm (1% of weight of fabric) |
| --- | --- | --- | --- |
| Woven fabric - Plain | 130.5 | 128.8 | 126.3 |
| Knits fabric - Single Jersey | 129.3 | 131.2 | 123.5, yellowing observed in cabinet |
| Terry Towel fabric | 131.4 | 130.3 | 121.3, visual yellowing observed |

Measure

1. The difference in whiteness index value when compared with untreated fabric is <3 units means no yellowing
2. The difference in whiteness index value when compared with untreated fabric is >3 and <8 unit means significant visual yellowing will be seen in colour matching cabinet under UV light
3. The difference in whiteness index value when compared with untreated fabric is >8 units means visual yellowing will be observed under sun light Inference from Results The inventive material in the experiment shows no yellowing on all types of fabric constructions when dried at 120 deg C.

f) CIE Whiteness Index (WI-CIE), ASTM whiteness Index (WI-ASTM), and yellowness Index (YI-E313) using Spectrophotometer (index D65 illuminate) measured for the cotton fabric treated with as-prepared product of Example 1 at the application conditions given below:

| Application conditions | |
| --- | --- |
| Fibre Type | 100% Cotton |
| application method | padding |
| pickup | 80% |
| pH of bath | 8.0 |
| Drying condition | 100° C. for 5 minutes |
| Dosage | undiluted, as prepared |

TABLE 2

Whiteness and yellowness indices for untreated control and treated cotton fabric.

| Sample | WI-ASTM | WI-CIE | YI-E313 |
| --- | --- | --- | --- |
| Control white cotton (plain weave, unfinished) | 73.21 | 74.33 | 3.46 |
| Treated cotton woven fabric with blue coloured aqueous dispersion of silver nanoparticles of Example 1 | 133.81 | 125.81 | N/A |

Inference from Results

Increase in WI both by CIE and ASTM methods on treatment of cotton fabric with the blue coloured aqueous dispersion of silver nanoparticles of Example 1 indicates that the material of present invention also acts as brightening agent for white fabrics.

g) Antibacterial response of cellulosic substrates treated with Blue silver dispersion along with different agents.
Method used—ASTM E-2149
Bacterium Used—E-Coli The material of present invention with surfactant gives 99.9% antimicrobial activity at an application of 0.1 ppm and a durability of up to 99.9% activity for up to 20 harsher washes (AATCC 61 II A).

TABLE 3

Antimicrobial activity of Blue coloured Ag nanoparticle dispersion treated polyester fabric

| S. No. | % of blue silver Product (of example 1) in aqueous medium (ppm application) | Additive added to blue silver dispersion | Antimicrobial activity (% reduction of colonies) | | | |
|---|---|---|---|---|---|---|
| | | | Un washed | after 10 washes | after 20 washes | after 30 washes |
| 1 | 1% (0.1 ppm) | without additive | 99.9% | 80% | 50% | 30% |
| 2 | 1% (0.1 ppm) | Wetting agent, mixture of alcohol ethoxylates (0.1 to 1% w/w) | 99.9% | 99.9% | 80% | 50% |
| 3 | 1% (0.1 ppm) | Cationic Surfactant dosage of (0.1 to 1% w/w) | 99.9% | 99.9% | 99.9% | 85% |
| 4 | 1% (0.1 ppm) | Epichlorohydrin-bishexamethylenetriamine polymer based binder dosage of (0.1 to 1.0% w/w) | 99.9% | 99.9% | 99.9% | 85% |
| 5 | 1% (0.1 ppm) | Acrylic Copolymer binder dosage of (0.1 to 1% w/w) | 99.9% | 99.9% | 98% | 80% |
| 6 | 1% (0.1 ppm) | Polyester resin dosage of (0.1 to 1% w/w) | 99.9% | 99.9% | 95% | 80% |

(Products show bacteriostatic effect with no zone of inhibition)

The product even when diluted to 1-2% (i.e. dilution up to two orders of magnitude) gives high antimicrobial activity compared to that known in prior art.

Prior art showed, 1000 ppm of nanosilver (average particle size 100 nm) is required to be applied on cotton fabric, for obtaining washing durability of up to 20 washes with 99.9% activity. (Pranee Rattanawaleedirojn Kanokwan Saengkietiyut, and Supin Sangsuk, J. Nat. Sci. Special Issue on Nanotechnology (2008) Vol. 7(1)) One of the other prior art showed 60 ppm of nanosilver (size 10-35 nm) application on silk fabric at 40 degree C. by exhaust method. It was found that after 10 washing cycles antimicrobial activity came down to 78% from 100% (before wash) (M. L. Gulrajani, Deepti Gupta, S. Periyasamy, S. G. Muthu, Journal of Applied Polymer Science, Vol. 108, 614-623 (2008))

Another study of the prior art showed 50 ppm of nanosilver application was necessary on woven cotton fabric to give 99.9% antimicrobial activity. The activity reduced to 90.1% after 20 mild washing cycles ( )ATCC 61-IA) and For polyester 50 ppm gave antimicrobial activity of only 91.6% (without wash) to 84.3% (after 20 washes) (H. J. LEE, S. Y. YEO, S. H. JEONG, JOURNAL OF MATERIALS SCIENCE 38 (2003) 2199-2204).

7. Colour Change of the Substrates

The product when applied at any concentration 1-100% gives no perceptible colour change to even lightly coloured substrates such as white textiles or pale shade dyed textiles.

8. Fixation Without Binder by Pad-Dry and Cure Method:

The above composition may be fixed without the use of optional binder by heat treating the padded fabric/substrates at temperatures greater than 120 deg C. to give significantly higher wash fastness than that reported in S. No. 1 of Table 3 above.

TABLE 4

Antibacterial activity of cotton treated with as-prepared blue coloured aqueous dispersion of Ag nanoparticle of Example 1 and cured at different conditions (washing standard used: AATCC-61-IIA **)

| Concentration of | Material Treated with blue coloured aqueous dispersion of silver | Antibacterial activity (%) | |
|---|---|---|---|
| | | Without wash | After 20 washes |
| Bacterial culture (S. aureus) | nanoparticles of Example 1 of the present invention | | |
| $10^5$ CFU/ml | Treated cotton only dried at 80° C. for 5 min | 93.3% | 82.72% |

TABLE 4-continued

Antibacterial activity of cotton treated with as-prepared blue coloured aqueous dispersion of Ag nanoparticle of Example 1 and cured at different conditions (washing standard used: AATCC-61-IIA **)

| Concentration of | Material Treated with blue coloured aqueous dispersion of silver | Antibacterial activity (%) | |
|---|---|---|---|
| | | Without wash | After 20 washes |
| Bacterial culture (*S. aureus*) | nanoparticles of Example 1 of the present invention | | |
| | Treated cotton dried at 80° C. for 5 min & cured at 120° C. for 5 min | 95.72% | 92.2% |
| | Treated cotton dried at 80° C. for 5 min & cured at 150° C. for 3 min | 99.99% | 97.4% |

The results show that when treated fabric with blue coloured aqueous dispersion of silver nanoparticles of the present invention is subjected to heat treatment at 120-150 deg C., the durability of the applied nanosilver finish increases significantly without the use of binders.

ADVANTAGES OF THE INVENTION (a) The aqueous dispersion of silver nanoparticles of the present invention is blue in colour, has majority of silver particles that are very small in size (in the rage 0.5-6 nm), and can combine the effect of antimicrobial finish and bluing/brightening agent used for brightening the white and pale coloured substrates.

(b) It shows 99.99% antimicrobial activity at very low concentrations.

(c) It is easy to synthesize directly in aqueous media and is stable at high temperature and in presence of sunlight.

(d) The dispersion stability of the silver nanoparticles of present invention is 15-24 months in normal room conditions.

(e) The silver particles provide wash durability after application on textile, binding with simple heat treatment at temperatures greater than 120 degree C. or with binders at room temperature.

(f) The dispersion has very high compatibility with binders and surfactants of various types.

(g) The silver particles have higher fixation to polymeric substrates as compared to the processes and products of the prior art.

(h) No yellowing was observed when applied on different construction of cotton finished fabrics when dried at 120-150 deg C. Brightness or improvement in whiteness index can be observed when drying condition is kept in the range of 30-100 deg C.

We claim:

1. An aqueous dispersion of silver nanoparticles, said dispersion comprising silver
    nanoparticles of anisotropic shape with at least 65% of the particles having equivalent diameter in range of 0.5 to 6 nm; said dispersion having plasmonic peaks in the range of 330 to 335 nm and 650 to 720 nm and an absence of plasmonic peaks in the range 390 to 410 nm and 410 to 500 nm in UV-Vis spectrum;
    said dispersion having molar extinction coefficient in the range of 10.1 mM$^{-1}$ cm$^{-1}$ to 15.7 nM$^{-1}$ cm$^{-1}$ at wavelength of maximum absorption in the range of 650-720 nm;
    said dispersion having storage stability of 15 to 24 months, and having Minimum Bactericidal Concentration (MBC) in the range of 0.055 to 0.099 ppm against gram positive bacteria,
    wherein said dispersion of silver nanoparticles is blue in colour.

2. A process for preparation of blue coloured aqueous dispersion of silver nanoparticles, the process comprising the steps of:
    (i) adding a protecting agent to a silver precursor solution to obtain a second solution;
    (ii) adding a stabilizer and hydrogen peroxide to the second solution of step (i);
    (iii) heating solution of step (ii) to a temperature in the range of 50 to 90 degree C.;
    (iv) reducing the heated solution of step (iii) with a reducing agent to obtain the blue coloured aqueous dispersion of silver nanoparticles;
    wherein the protecting agent is selected from the group consisting of poly(ethylenediamine), sodium acetate, bis(p-sulfonatophenyl)phenyl phosphine dipotassium dihydrate, polythene glycol, polyvinyl alcohol and polyvinyl pyrrolidone;
    wherein the stabilizer is selected from the group consisting of ethylenediamine tetra acetate salt, nitriloacetic acid salt and trisodium citrate;
    wherein the reducing agent is selected from the group consisting of ascorbic acid, sodium tri-sec-butylborohydrate, lithium aluminum hydride, potassium tri-sec-butyl borohydride, potassium triethylborohydride, sodium triacetoxy borohydride and sodium borohydride; and
    wherein the silver nanoparticles have an anisotropic shape with at least 65% of the particles having equivalent diameter in range of 0.5 to 6 nm.

3. The process as claimed in claim 2, wherein a surfactant is optionally added at any step before step (iv).

4. The process as claimed in claim 2, wherein the silver precursor is selected from the group consisting of silver nitrate, silver perchlorate, silver acetate, silver sulphate and silvertetraoxy-chlorate.

5. The process as claimed in claim 2, wherein the silver precursor is silver nitrate.

6. The process as claimed in claim 2, wherein the protecting agent is polyvinyl pyrrolidone.

7. The process as claimed in claim 2, wherein the stabilizer is trisodium citrate.

8. The process as claimed in claim 2, wherein the reducing agent is sodium borohydride.

9. The process as claimed in claim 3, wherein the surfactant is selected from the group consisting of anionic and non ionic surfactants including sodium dodecyl sulfate (SDS), polysorbates, sodium salts of polyacrylic acids, and salts of alkylbenzo sulphonates and its condensates.

10. The process as claimed in claim 2, wherein the mole ratio of silver precursor to protective agent is in the range of 1:0.1-1:100.

11. The process as claimed in claim 2, wherein the mole ratio of silver precursor to stabilizer ranges from 1:1 to 1:100.

12. The process as claimed in claim 2, wherein the mole ratio of silver precursor to reducing agent is in the range of 1:8.5 to 1:50.

13. The process as claimed in claim 2, wherein the mole ratio of silver precursor to hydrogen peroxide is in the range of 1:50 to 1:500.

14. The process as claimed in claim 3, wherein the mole ratio of silver precursor to surfactant is in the range of 1:0.5 to 1:350.

15. The process as claimed in claim 2, wherein optionally either a binder or a surfactant or both are added to the blue coloured aqueous dispersion of silver nanoparticles.

16. An aqueous composition comprising 1-99 wt % of aqueous dispersion of blue coloured silver nanoparticles as claimed in claim 1, 0.001 to 10 wt % of a surfactant optionally with 0.1 to 10 wt % of a binder of the final composition.

17. A composition comprising 1-99 wt % of aqueous dispersion of blue coloured silver nanoparticles as claimed in claim 1, and a binder, wherein the binder is in the range of 0.1 to 10 weight % of the final composition.

18. The composition as claimed in claim 16, wherein the surfactant is selected from the group consisting of anionic and non ionic surfactants including sodium dodecyl sulfate (SDS), polysorbates, sodium salts of polyacrylic acids, and condensates of benzo sulphonic acids or a mixture of any two or more selected from the group.

19. The composition as claimed in claim 16, wherein the surfactant is sodium dodecyl sulfate (SDS).

20. The composition as claimed in claim 16, wherein the binder is selected from the group consisting of acrylic based binder, epichlorohydrin-bishexamethylenetriamine based binder, copolymer binder with maleic acid, epoxy based binders, polyurethane and polyester resin based binders.

21. The composition as claimed in claim 16, wherein the binder is Epichlorohydrin bishexamethylenetriamine based binder.

22. The compositions as claimed in claim 16, wherein the minimum bactericidal concentration (MBC) are in the range of 0.055 to 0.01 ppm.

23. The composition as claimed in claim 16, wherein the molar extinction coefficient is in the range 14.1-19.0 $mM^{-1}$ $cm^{-1}$.

24. The compositions as claimed in claim 16, gives no yellowing effect when applied on cotton fabrics at 120 deg C.-150 deg C. and gives whiteness index higher than the control fabric by 10-85% when applied on fabric at 30-100 deg C.

* * * * *